(12) United States Patent
Mathis

(10) Patent No.: US 7,048,436 B2
(45) Date of Patent: May 23, 2006

(54) METHOD AND APPARATUS FOR MONITORING SUBSTANCES

(75) Inventor: Nancy Mathis, Fredericton (CA)

(73) Assignee: Mathis Instruments Ltd., New Brunswick (CA)

(*) Notice: Subject to any disclaimer, the term of this patent is extended or adjusted under 35 U.S.C. 154(b) by 9 days.

(21) Appl. No.: 10/482,049

(22) PCT Filed: Jun. 27, 2002

(86) PCT No.: PCT/CA02/00962

§ 371 (c)(1),
(2), (4) Date: Dec. 22, 2003

(87) PCT Pub. No.: WO03/002998

PCT Pub. Date: Jan. 9, 2003

(65) Prior Publication Data
US 2004/0165645 A1    Aug. 26, 2004

Related U.S. Application Data

(60) Provisional application No. 60/300,838, filed on Jun. 27, 2001.

(51) Int. Cl.
G01N 25/00 (2006.01)

(52) U.S. Cl. .......................... 374/43; 374/45

(58) Field of Classification Search ................ 374/43, 374/44, 45, 53; 366/142, 151.1, 17, 152.1, 366/76.2; 700/265; 137/3, 4, 5, 88, 91, 137/92, 93
See application file for complete search history.

(56) References Cited

U.S. PATENT DOCUMENTS 3,789,654 A * 2/1974 Jones .......................... 374/43

(Continued)

FOREIGN PATENT DOCUMENTS

WO    WO 99/24814    5/1999

(Continued)

OTHER PUBLICATIONS

Thermal Conductivity Homogeneity and Topography Characterization, Nancy Mathis et al, Semiconductor Thermal Measurement and Management Symposium, Mar. 1999, pp. 1-6.

Primary Examiner—Diego Gutierrez
Assistant Examiner—Mirellys Jagan
(74) Attorney, Agent, or Firm—Carmody & Torrance LLP

(57) ABSTRACT

The methodology disclosed permits the testing of fluids, solids, powders and pastes through the measurements of effusivity. Effusivity is a measurement that combines thermal conductivity, density, and heat capacity. Blend uniformity, homogeneity, miscibility, concentration, voiding\delamination, and moisture content are exemplary of the applications to which the present methodology is applicable. The method of monitoring homogeneity, miscibility, concentration, voiding\delamination, and moisture content in a material comprises the steps of measuring effusivity of a first portion of the material, measuring effusivity of a second portion of the_material, comparing each measurement. The caparison may be between the measurements themselves or to a predetermined range of values and indicating which portion has an out of range measurement. The method of monitoring blend uniformity in a mixture containing a plurality of components to be mixed, comprises the steps of providing a first composition and a second composition, each having a different effusivity, mixing said first composition and said second composition, measuring effusivity in said mixture during mixing, determining the relative standard between measurements, and correlating the relative deviation for a determination of blend uniformity.

5 Claims, 5 Drawing Sheets

U.S. PATENT DOCUMENTS

| | | |
|---|---|---|
| 3,822,580 A | 7/1974 | Jamet et al. |
| 3,951,386 A | 4/1976 | Small et al. |
| 4,027,524 A * | 6/1977 | Fletcher et al. ............... 374/43 |
| 4,171,164 A * | 10/1979 | Groves et al. ........... 366/152.1 |
| 4,928,254 A | 5/1990 | Knudsen et al. |
| 5,795,064 A | 8/1998 | Mathis |
| 5,946,088 A * | 8/1999 | Aldridge .................... 356/300 |
| 6,195,443 B1 * | 2/2001 | Hammond et al. ......... 382/100 |
| 6,690,016 B1 * | 2/2004 | Watkins et al. .......... 250/341.7 |
| 6,791,688 B1 * | 9/2004 | Lai et al. .................... 356/417 |
| 6,874,928 B1 * | 4/2005 | Afnan et al. ................ 366/142 |
| 2004/0008570 A1 * | 1/2004 | Folestad et al. ............ 366/142 |

FOREIGN PATENT DOCUMENTS

| | | |
|---|---|---|
| WO | WO 00/36410 | 6/2000 |

* cited by examiner

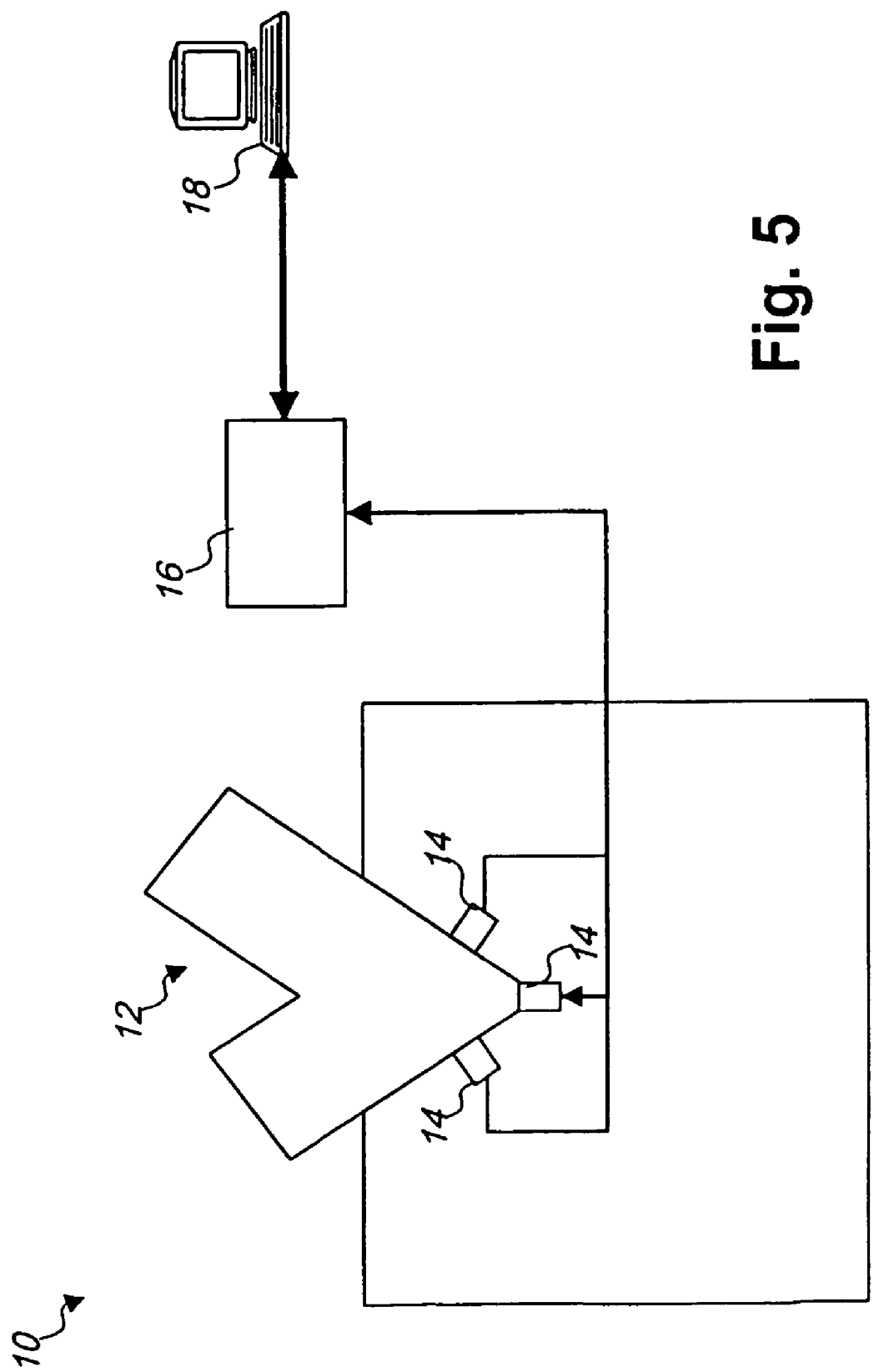

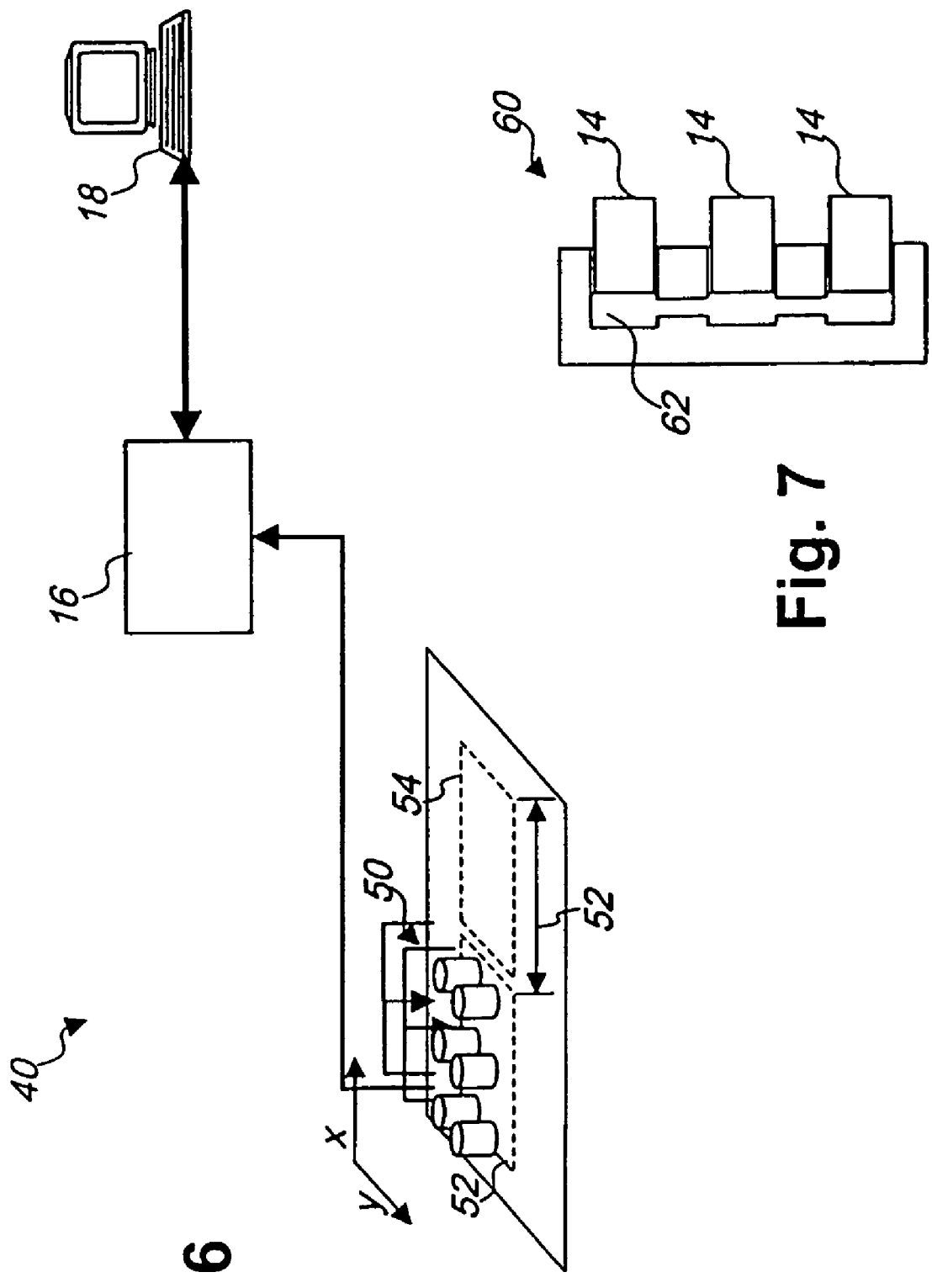

METHOD AND APPARATUS FOR MONITORING SUBSTANCES

This is a 371 of PCTCA/02/00962, filed Jun. 27, 2002, which claims priority to and the bendfit of provisional application Ser. No. 60/300,838, filed Jun. 27, 2001.

FIELD OF THE INVENTION

The present invention relates to a method and apparatus for monitoring substances and in particular monitoring uniformity in a mixture to ensure proper blending.

BACKGROUND OF THE INVENTION

Effusivity is a measurement that combines thermal conductivity, density, and heat capacity.

The effusivity of a material (sometimes called thermal inertia) is the square root of the product of the thermal conductivity, density and heat capacity. The effusivity of your hand and the object it touches determines the interfacial surface temperatures of your hands. If the effusivity of a material is high-as with ceramic, the interfacial temperature is lower than if the effusivity is lower-as with wood. This is why a wood floor feels warmer than a ceramic floor, and why a carpeted floor feels warmer still.

As a natural characteristic of materials, each has a different effusivity from the other. Effusivity is sensitive to composition in view of the fact that materials differ in value from 5 $Ws^{1/2}/m^2K$ for air to several thousand for advanced composites.

In order to measure effusivity, a suitable probe such as that provided for U.S. Pat. No. 5,795,064, issued Aug. 18, 1998, to Mathis, may be used, the entire disclosure of which is hereby incorporated by reference.

In the pharmaceutical industry, when powdered components are blended during drug production, time is a critical factor. Typically, when a drug formulation is developed, bench-scale amounts are synthesized and subsequently scaled up through a series of steps to 1000 kg blending equipment. One of the key limitations in the field is that optimum mixing time of the components has to be established by trial and error. Blending for an insufficient amount of time fails to mix the samples, while over blending causes segregation. It is also a significant problem that over blending is time consuming and the added frictional heat can thermally damage the sensitive components in the mixture.

SUMMARY OF THE INVENTION

An object of the present invention is to provide an improved method and apparatus for monitoring substances The methodology disclosed herein permits the testing of fluids, solids, powders and pastes. Blend uniformity, homogeneity, miscibility, concentration, voiding/delamination, and moisture content are exemplary of the applications to which the present methodology is applicable.

The instant methodology permits an on-line, in situ, real-time measurement to determine the optimum blending time.

In accordance with one aspect, the present invention seeks to improve the blending art, and, by the present methodology, many of the significant limitations, particularly those realized in the pharmaceutical industry, are overcome.

In accordance with aspect of the present invention there is provided a method of monitoring blending in a mixture containing a plurality of components compositions to be mixed, the steps of:

providing a first composition and a second composition, each having a diffrent effusivty;

mixing the first composition and the second composition;

measuring one or more than one first effusivity in the mixture during mixing;

after the measuring step, further measuring one or more than one second effusivity in the mixture during the mixing;

determinig the relative deviation between the first effusivity and the second effusivity; and determining blend uniformly in dependence upon correlating the relative deviation to a predetermined value.

In accordance with another aspect of the present invention there is provide a method of monitoring a material comprising the steps of measuring effusivty of a first portion of the material, measuring effusivity of a second portion of the matererial and statistically comparing each measurement.

BRIEF DESCRIPTION OF THE DRAWINGS

The present invention will be further understood from the following detailed description with reference to the accompanying drawings in which:

FIG. 5 illustrates in a block diagram apparatus in accordance with one embodiment of the present invention;

FIG. 6 illustrates an apparatus similar to that of FIG. 5, with the sensors arranged in an array in accordance with a second embodiment of the present invention;

FIG. 7 illustrates a sensor array for non-planar surfaces in accordance with a third embodiment of the present invention;

Similar numerals denote similar elements throughout the drawings.

DETAILED DESCRIPTION OF THE PREFERRED EMBODIMENTS

Figure 1:
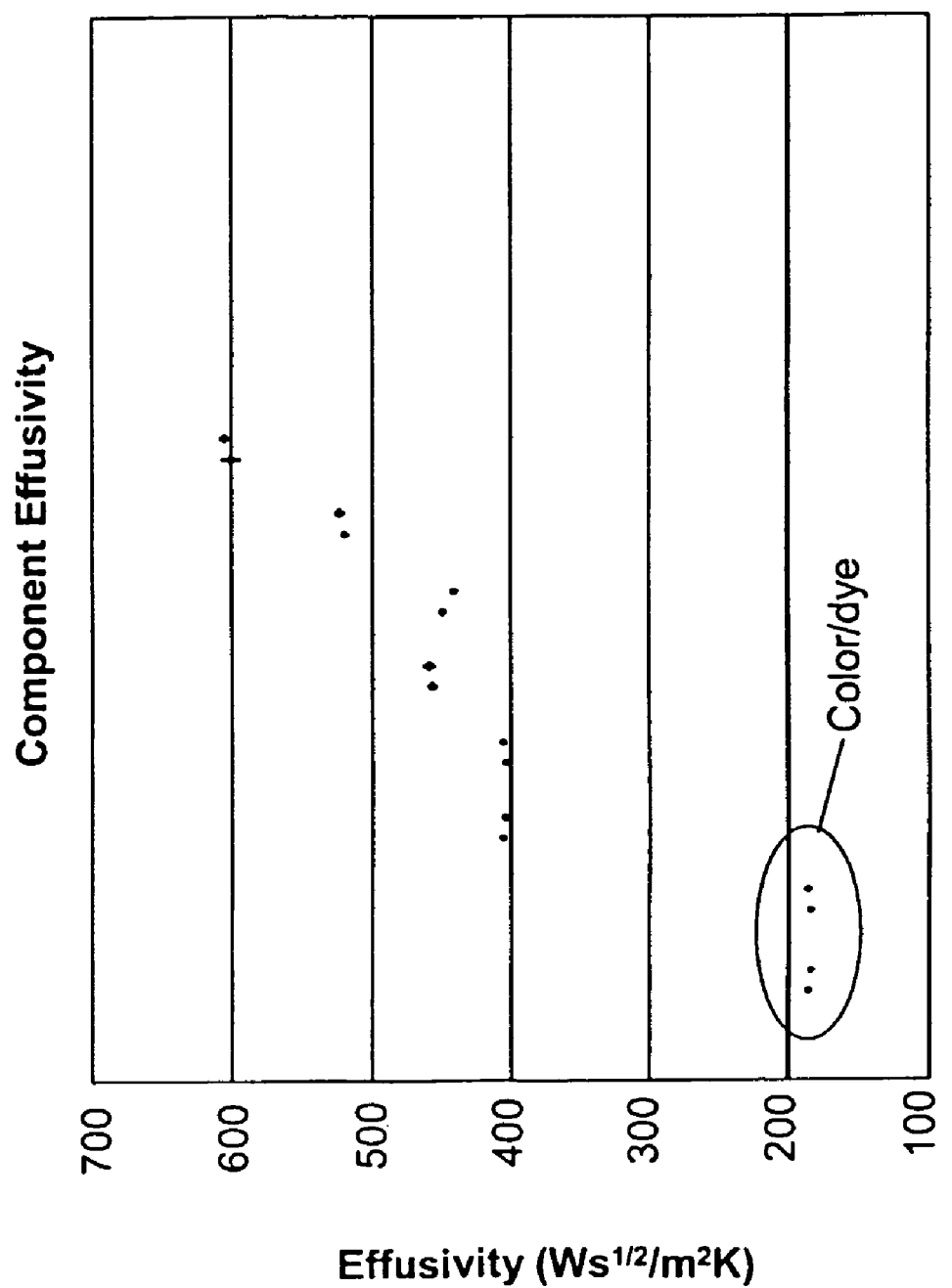
FIG. 1 graphically illustrates representation of the effusivity for eight different materials.

Referring to FIG. 1 there is graphically illustrated component effusivity where effusivity is illustrated as a function of the material.

Eight components of a commercially available formulation were tested to determine if the effusivity values were distinct enough to permit differentiation.

Figure 2:
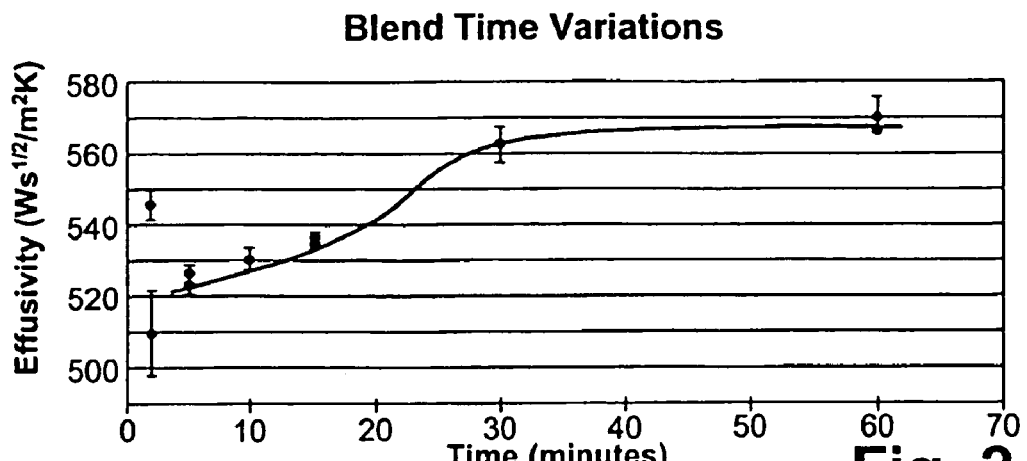
FIG. 2 graphically illustrates effusivity as a function of time during blending of eight components of FIG. 1.
Figure 3:
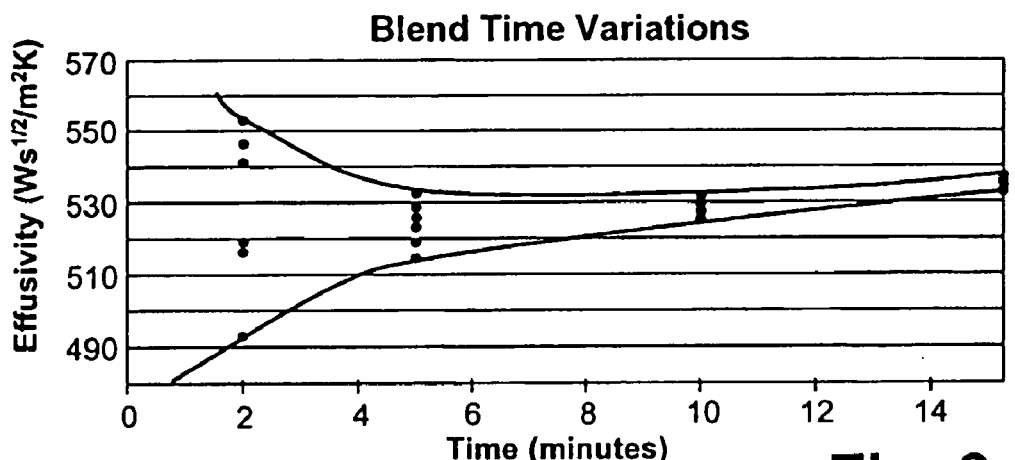
FIG. 3 graphically illustrates effusivity as a function of time where the time-scale of FIG. 2 is enlarged to show variations of effusivity.
Figure 4:
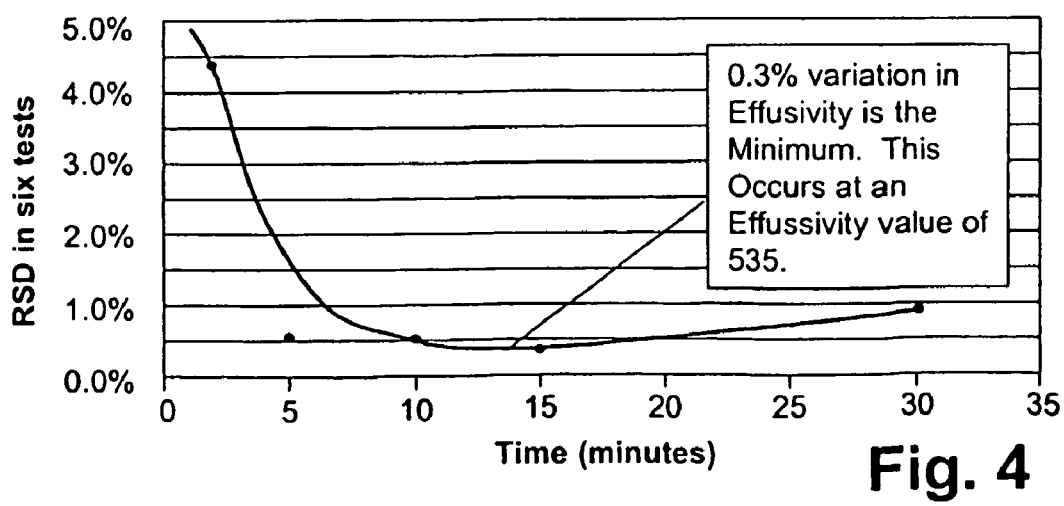
FIG. 4 graphically illustrates relative standard deviation of effusivity as a function of blend time for the blending of FIG. 2 and FIG. 3.

Several grams of each material were placed in a vial and each point on the graphical illustrations in FIGS. 2, 3, and 4 were the result of triplicate testing conducted on one aliquot from the vial. The triplicate tests had an average relative standard deviation of 0.6%. Two aliquots were tested and the variance between the two was under 6.1%.

Two colour/dye components were indistinguishable, but the next closest effusivity value was 225% higher. The effusivity spanned from 180 to over 600 $Ws^{1/2}/m^2K$, thus indicating that effusivity of a blend of these components would be sensitive to uniformity.

The components discussed above were subsequently blended and samples extracted at times from 2 minutes through 60 minutes.

Referring to FIG. 2 there is graphically illustrated effusivity as a function of time during blending of eight components of FIG. 1. FIG. 2 tabulates the testing results. Each point on the graph is the result of triplicate testing from one aliquot from the vial. The triplicate had an average relative standard deviation of 0.6% which was exactly in agreement with the component testing phase. The trend in the average results is to increase and then level off. Two aliquots were tested and the variance between the two ranged from 6.4% down to 0%.

Referring to FIG. 3 there is graphically illustrated effusivity as a function of time where the time-scale of FIG. 2 is enlarged to show variations of effusivity. FIG. 3 shows the time scale in the first 15 minutes of blending. The data illustrates the six individual results rather than the average. The first sample drawn at 2 minutes had a large scatter in the results due to the non-uniformity in the blend. As time progresses towards 15 minutes, it is evident from the convergence of maximum and minimum curves that the repeatability improves and is an indication of the uniformity.

Referring to FIG. 4, there is graphically illustrated relative standard deviation of effusivity as a function of blend time. The minimum in FIG. 4 at approximately 15 minutes is indicative of a uniform blend. While relative standard deviation is plotted in the graph of FIG. 4, other statistically appropriate mathematical analyses of the measurements could be used that would yield relative deviation of measurements as will be appreciated by those of ordinary skill in the art.

Referring to FIG. 5, there is schematically illustrated an embodiment of the apparatus that could be used for the instant application. The blending apparatus is represented by a piece of blending equipment, for example a V-blender 12, modified by including three probes near the bottom of the V-blender, or more particularly, at the vertex of the blender and up the sides of the blender. The probes are coupled to a circuit 16, as is set forth in the U.S. Pat. No. 5,795,064. The circuit subsequently interfacing with a CPU, broadly denoted by numeral 18. As an option, the apparatus 10 may include a plurality of probes (i.e. more than three), the other probes are not shown in FIG. 5 with the probes being positioned at different locations on the body of the V-blender.

Where a plurality of probes 14 is incorporated, the information from the probes may be gathered simultaneously, i.e. each probe may simultaneously send its information to the CPU via the circuit 16 or the results may be spread out over a predetermined time frame.

In addition to determination of uniform blending as described herein above, the apparatus of FIG. 5, with multiple sensors as shown, can be used for determination of homogeneity of a substance, miscibility of substances. The apparatus of FIG. 5 could also be used to provide relative concentration indications and may be calibrated to provide concentration measurements.

Referring to FIG. 6, there is illustrated an apparatus similar to that of FIG. 5, with the sensors arranged in an array. If the sensors are arranged in a planar array 50 as illustrated, planar materials can be tested for uniformity of effusivity over a surface.

In operation, the array 50 is positioned on a first position 52 where a first measurement is taken for a predetermined time period, the array 50 is then translated a distance 54 to a second position 56, where a second measurement is taken for the predetermined time period.

Measurements from each probe 14 could be taken individually then arranged or a total measurement from all the probes 14 could be taken. By moving the array around repeating the measurements, any differences between individual probes are ameliorated through averaging. For horizontal surfaces gravity can be relied upon to provide a uniform pressure on the probe surface. Differences in the measurements over the surface can be correlated to physical differences through investigation of contributing factors. For example, if the planar material were plywood, variances in moisture content could be eliminated through separate moisture content tests using pin probes. Then dissection of the area showing a variance could proceed to determine if a void, delamination or shortage of glue was evident. The resulting physical investigation could then be used to "calibrate" the effusivity variation range attributable to different physical defects.

As mentioned in the above example, moisture content can affect the effusivity value, consequently the same planar array could be employed to check the moisture content of an otherwise substantially uniform surface. For example, a plasterboard wall could be checked without leaving pin marks, for moisture variations that might be used to determine readiness for purity or help locate a water leak. For such a non-horizontal application a uniform force would need to be applied to the array to ensure consistency between positions.

Referring to FIG. 7, there is illustrated a sensor array for non planar surfaces. By mounting the sensors 14 to form a flexible matrix a sensor array 60, can be used on curved surfaces. A similar effect may be possible through spring loading of each sensor, however the concern there would be the effect on measurements of variations in the loading of individual sensors. Fluidly coupled pistons supporting sensors would be able to be positioned without such variances as the hydraulic fluid 62 communication between each piston to that of the other sensor support piston would ensure uniform pressure.

Figure 8:
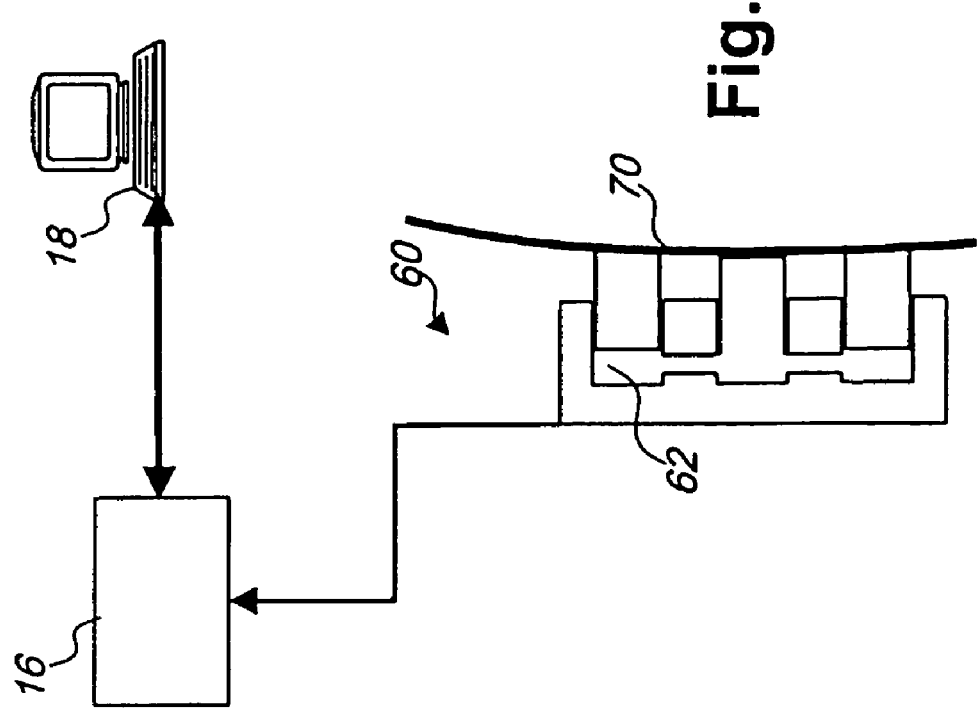
FIG. 8 illustrates the apparatus of FIG. 6 with the sensor array of FIG. 7.

Referring to FIG. 8, there is illustrated the apparatus of FIG. 6 with the sensor array of FIG. 7. One application for the probe array capable of conforming to a curved surface 70 would be the testing of vessels having hulls or fuselages where structural integrity is critical to their safe operation. For example, boats made of laminated material such as fiberglass reinforced polyester (GRP) may deteriorate over time due to delaminating or marine osmosis. With delaminating the individual layers of glass fiber cloth may separate over time due to stresses the boat is subjected to. In the case of marine osmosis water forms pockets between the gel coat layer (the smooth outer finish) of the hull and the structural layers formed by fiberglass cloth and/or matt. The infiltration of water happens over time to these vessels not treated with epoxy resin below the waterline.

Similarly, modern wooden boats built using wood laminates saturated with epoxy resin may have layers delaminate over time or may not be laminated properly during construction.

The array could be used to test boats for either delaminating or moisture content in a manner similar to that for the planar material of FIG. 7.

Again, some form of calibration of the array would be necessary for each application; such calibration is within the range of ordinary skill in the art.

Similarly, the skin of an aircraft fuselage and wing surfaces could be checked for uniformity using the sensor array described herein above.

Figure 9:
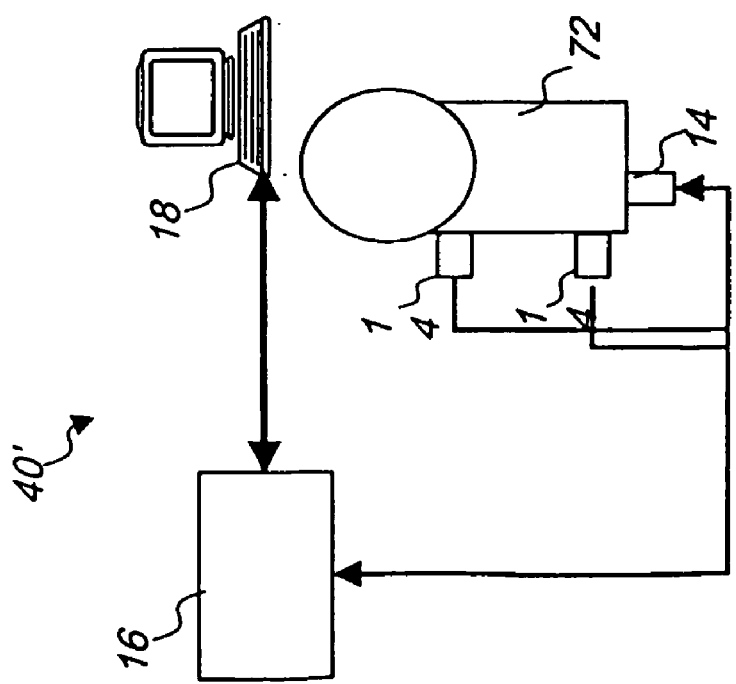
FIG. 9 illustrates apparatus similar to that of FIGS. 5, 6 and 8 in accordance with a fourth embodiment of the present invention.

Referring to FIG. 9, there is illustrated apparatus similar to that of FIGS. 5, 6 and 8. In the realm of substance homogeneity, there are also numerous applications for the apparatus 40 of FIGS. 5 and 6. For example apparatus 40, for monitoring the condition of essential fluids used in machinery could be achieved by positioning a sensor or sensors in fluid containing vessels, such as engine sump 72 or transmission cases. Over time, measurements could be made to determine measurement changes with a predetermined threshold or range indicating a need to change fluids in the case of a single sensor. For an array of sensors, oil in an engine sump could be checked as part of a startup routine to ensure sludge was not forming in the lower part of the sump, or that foreign fluids such as water or coolant, had not accumulated on top of the oil.

Consequently. the present methodology facilitates the detection of flaws, imperfections, inconsistencies, or non-uniformities in materials having an effusivity value. In particular, by measuring the relative deviation in the effusivity of values over time, it can be determined when optimum blending has occurred, in the case for blending. This methodology can be easily extrapolated to other industries; such as the integrated circuit manufacturing industry where delimitations between chip layers is important.

Although embodiments of the invention have been described above, it is not limited thereto and it will be apparent to those skilled in the art of numerous modifications form part of the present invention insofar as they do not depart from the scope of the invention as defined in the claims.

I claim:

1. A method of monitoring blending a mixture containing a plurality of compositions to be mixed, comprising the steps of:
   providing a first composition and a second composition, each having a different effusivity;
   mixing said first composition and said second composition;
   measuring one or more than one effusivity in said mixture during mixing;
   after said measuring step, further measuring one or more than one second effusivity in said mixture during said mixing;
   determining the relative deviation between one or more than one first effsivity and the one more than one second effusivity; and
   determining blend uniformty in dependence upon correlating the relative deviation to a predetermined value.

2. The method as set forth in claim 1, wherein said method is an on-line or in-line method.

3. The method as set forth in claim 2, wherein said measurements are obtained in real-time.

4. The method as set forth in claim 1, wherein said measuring step and said further measuring step are done at a plurality of locations in said mixture.

5. The method as set forth in claim 4, wherein each of said measuring step and said further measuring step is done at a plurality of locations is simultaneously.

* * * * *